United States Patent [19]
Bouquet et al.

[11] Patent Number: 5,153,231
[45] Date of Patent: Oct. 6, 1992

[54] SILICONE FOAMS

[75] Inventors: Philippe L. Bouquet, Mouans-Sartoux, France; David Pocknell, Rhoose, United Kingdom

[73] Assignee: Dow Corning France S.A., Valbonne, France

[21] Appl. No.: 849,855

[22] Filed: Mar. 12, 1992

[30] Foreign Application Priority Data

Mar. 13, 1991 [FR] France .................. 91 03016

[51] Int. Cl.$^5$ .................................... C08J 9/04
[52] U.S. Cl. ............................... 521/88; 521/97; 521/117; 521/130; 521/154; 424/447
[58] Field of Search ............ 521/88, 117, 130, 154, 521/97

[56] References Cited

U.S. PATENT DOCUMENTS

| | | | |
|---|---|---|---|
| 4,026,842 | 5/1977 | Lee et al. | 521/154 |
| 4,026,843 | 5/1977 | Kittle | 521/154 |
| 4,026,844 | 5/1977 | Kittle et al. | 521/154 |
| 4,026,845 | 5/1977 | Kim et al. | 521/154 |
| 4,550,125 | 10/1985 | Lee et al. | 521/154 |
| 4,613,630 | 9/1986 | Bauman et al. | 521/154 |
| 4,719,243 | 1/1988 | Pocknell | 521/127 |

FOREIGN PATENT DOCUMENTS 2589872 5/1987 France .

*Primary Examiner*—Morton Foelak
*Attorney, Agent, or Firm*—John L. Chiatalas

[57] ABSTRACT

A multi-component foamable silicone composition is described and claimed which is capable of curing quickly at 20° C. to provide a low density foamed mass. The composition comprises (A) one or more polydiorganosiloxanes having not less than three alkylhydrogensiloxane units per molecule, (B) one or more polydiorganosiloxanes having not less than two alkenylsiloxane units (C) a liquid alcohol, (D) a fluorinated silicone foam stabilizing material and (E) a platinum catalyst for promoting reaction between the components. The composition may be packaged as two or more individually stable parts of substantially equal volume and viscosity each in a receptacle of material which is adapted to be opened by rupture so as to release the components for admixture. The composition is intended for use in forming a foam medical dressing by dispensing onto a surface e.g. an open wound and allowing the composition to cure at room temperature.

7 Claims, 1 Drawing Sheet

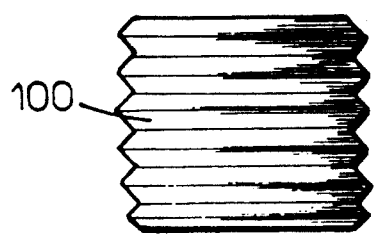
FIG.:1
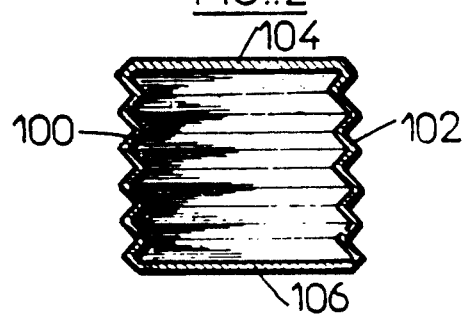
FIG.:2

SILICONE FOAMS

This invention is concerned with improvements in or relating to silicone foams.

Liquid curable compositions are available which flow and foam readily at room or slightly elevated temperature to provide a cured foam product. It has been proposed to employ foamable silicone based room temperature curable compositions for various purposes, including the preparation of medical dressings. Compositions for this purpose are disclosed for example, in French Patent Specification 2589872. The compositions referred to therein comprise an organosilicon polymer including siloxane units providing a silicon-bonded hydroxyl group, an organosilicon polymer including siloxane units having a silicon-bonded hydrogen atom, a catalyst, for example a tin compound, and finely divided filler comprising silica which has been treated to render it hydrophobic. The compositions cure according to the scheme ≡SiOH + ≡SiH→≡Si-O-Si≡ +H$_2$.

Whilst satisfactory in many ways, the tin catalysed compositions disclosed in French Patent Specification 2589872 are regarded as less than satisfactory in that it has been suggested that the tin compound catalysts and/or derivatives thereof may have some undesirable toxic effects.

Formulations have been proposed for silicone rubber foams which do not use tin compound catalysts. Many of these formulations employ polydiorganosiloxanes having silicon-bonded vinyl groups available for reaction with polydiorganosiloxanes having silicon bonded hydrogen atoms and a platinum catalyst. The addition reaction which occurs is appropriate to yield chain extended or crosslinked elastomeric silicone products, but does not generate volatile materials for causing foaming in the curing composition. A foaming reaction may be induced in such formulations by inclusion of a polydiorganosiloxane having silicon-bonded hydroxyl groups among the ingredients with a view to reaction with the polydiorganosiloxane having silicon-bonded hydrogen atoms as more fully described for example in U.S. Pat. No. 4,026,845, with or without the presence of water or an aliphatic alcohol as more fully described for example in U.S. Pat. No. 4,613,630, or by inclusion in the composition of a volatile blowing agent as more fully described for example in U.S. Pat. No. 4,550,125. Hitherto, our attempts to employ foamable compositions based on polydiorganosiloxanes having silicon bonded hydrogen atoms and silicon-bonded vinyl groups have not resulted in compositions which cure and foam suitably to form foamed dressings in situ on a patient's body. In particular they do not always cure satisfactorily in contact with wet wound surfaces and may even exhibit an uncured, liquid surface layer; some cure too slowly for convenient use and others do not yield a foam of desirably low density and structure for convenient use as an in situ formed medical dressing. It is believed that the failure to cure at the surface of the foam is due to interference by water present on the surface with the balance of hydroxy reactants and SiH groups required for desired platinum catalysed curing and foaming reactions. Desirably, compositions intended for in situ provision of medical dressings are curable at room temperatures of the order of 20° C. ± 4° C. within 100 seconds ± 40 seconds of application to the body to yield a foam of uniform fine pores having a density between 100 Kg/m$^3$ and 400 Kg/m$^3$ and having a major proportion of open cells. Further, medical dressings are generally applied by nursing staff and it is desirable to provide the composition in a form which is easily and consistently applied using a simple manual technique. Existing techniques include simple mixing of the components in an open container when required for use. Attempts to provide such compositions in a form suitable for mixing in a simple hand operated or aerosol device have been generaly unsuccessful, particularly in those cases where one of the components has a significantly different viscosity from another, as may occur for example when one of the components consists of or contains a volatile blowing agent which is intended to vaporise and assist in formation of the foam. It is believed that compositions supplied in two or more parts for mixing in a mixing device should comprise parts of substantially the same viscosity and this imposes some limitations on the materials available for use in such compositions and imposes requirements on the formulation of the individual component parts of the composition. It is also desirable that the component parts be of at least substantially the same volume in order to ensure consistent mixing of the ingredients in correct proportions.

It is one of the various objects of the present invention to provide an improved foamable silicone composition which may be readily mixed, for example in a hand held mixing and dispensing device, and dispensed to form a low density foam which is suitable for use as a medical dressing, for example by direct application to the human or animal body.

We have now found that an improved platinum catalysed silicone foam composition suitable for application direct to the human or animal body may comprise or consist of a selected blend of vinylpolysiloxane, hydrogenopolysiloxane, certain materials having carbon-bonded hydroxyl groups and a platinum catalyst. We have also found that when packaged in appropriate form the composition may be stored, mixed in, and dispensed in sterile condition from a hand held mixing device adapted to be held in one hand of an operator.

The present invention provides in one of its aspects a multi-component foamable silicone composition, capable on admixture of its component parts of curing quickly at 20° C. to provide a foamed mass having a density of less than 400 kg/m$^3$ comprising (A) one or more polydiorganosiloxanes having not less than three alkylhydrogensiloxane units per molecule, (B) one or more polydiorganosiloxanes having not less than two siloxane units of the formula

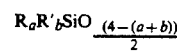

in which R represents a monovalent hydrocarbon group containing 1 to 20 carbon atoms, R' represents an unsaturated hydrocarbon group, a has the value 0, 1 or 2 and b has the value 1 or 2, (C) a liquid alcohol, (D) a fluorinated silicone foam stabilizing material and (E) a platinum catalyst for promoting reaction between the components, the composition being packaged as two or more individually stable parts of substantially equal volume and viscosity each in a receptacle of material which is adapted to be opened by rupture so as to release the components for admixture.

Foamable compositions according to the invention foam and cure by chemical reaction between the components (A), (B), and (C). Reaction between (A) and (B) results in a network of interconnected polysiloxane chains, and reaction between (A) and (C) generates hydrogen gas which serves to form cells within the developing network. The foam stabilizing material (D) serves to ensure that the cured foam has a desired structure. The polydiorganosiloxanes and other ingredients and the proportions thereof are selected so that the network is sufficiently developed and cured to produce a resilient foam of desired cellular structure within a short period of time of the order of three minutes or less after mixing.

Suitable polydiorganosiloxanes having alkylhydrogensiloxane units include polymers having units according to the general formula

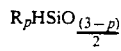

in which each R represents a monovalent hydrocarbon group containing 1 to 20 carbon atoms, for example, a lower alkyl e.g. a methyl, ethyl or propyl group or a phenyl group, and p is 1 or 2. The alkylhydrogen polydiorganosiloxanes may also comprise units $$R_nSiO_{\frac{(4-n)}{2}}$$  (i)

in which R is as referred to above and n is 1, 2 or 3. Preferably this polydiorganosiloxane has from 0.5% to 2.5% by weight of silicon-bonded hydrogen atoms. We prefer that each R represents a methyl group (Me). Preferably, terminal groups of the alkylhydrogen polydiorganosiloxane have the formula $Me_3SiO_{\frac{1}{2}}$. Suitable alkylhydrogen polydiorganosiloxanes include those comprising MeHSiO units with or without the presence of $Me_2SiO$ units and having viscosities of the order of from about 1 to about 1000 mm$^2$/s more preferably from about 5 to about 50 mm$^2$/s. Mixtures of such polydiorganosiloxanes may be used.

A composition according to the invention includes a polydiorganosiloxane (B) having two or more siloxane units having silicon-bonded unsaturated hydrocarbon groups R', for example cyclohexenyl or a group R"CH=CHR"', where R" may be absent or represents a divalent hydrocarbon group and R''', represents a hydrogen atom or an alkyl group; for example the unsaturated hydrocarbon group R' may be a vinyl, allyl or hexenyl group. These polydiorganosiloxanes also comprise units (i) in which R and n are as referred to above. As with the polydiorganosiloxane (A) the R groups of the various siloxane units of polydiorganosiloxane (B) represent a monovalent hydrocarbon group containing 1 to 20 carbon atoms, and are preferably methyl groups. These materials are reactive with the silicon-bonded hydrogen atoms in presence of the platinum catalyst by a hydrosilylation reaction to form the polysiloxane matrix. Preferably, these polydiorganosiloxanes have from 0.001% to 1% by weight of aliphatically unsaturated groups and a viscosity of the order of about 10 mm$^2$/s to about 25,000 mm$^2$/s. More preferably their viscosity lies in the range 100 mm$^2$/s to 10,000 mm$^2$/s. If desired, mixtures of polydiorganosiloxanes (B) which have different contents of unsaturated groups or different viscosities may be used.

A composition according to the invention also includes one or more liquid alcohols (C). These materials influence the structure of foams formed by use of the composition and have a significant influence on the density of the cured foam. The alcohol is selected with a view to contributing not only generation of hydrogen gas but also with a view to achieving desired softness and resilience of the foam. Suitable alcohols include the primary aliphatic and araliphatic alcohols for example the lower aliphatic monofunctional alcohols having up to 8 carbon atoms, e.g. ethanol, n-propyl alcohol and benzyl alcohol. Foams of lowest density are formed by use of the aliphatic alcohols having from 2 to 12 chain carbon atoms.

If desired other materials having hydroxyl groups reactive with the silicon-bonded hydrogen atoms may also be employed but it is important to ensure that their inclusion does not lead to unacceptable loss of hydrophobicity of the composition. Such other materials may be, for example, a silanol e.g. diphenylmethylsilanol or silanol terminated polydioganosiloxanes according to the general formula $HO((R_2)SiO)_sH$ in which each R is as aforesaid and is preferably a methyl group and s has a value from about 10 to about 40. Suitable materials have viscosities of the order of about 50 mm$^2$/s to about 2500 mm$^2$/s, or may be for example, polydiorganosiloxanes having at least two siloxane units of the formula

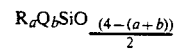

in which Q represents a hydroxyl bearing alkylene or oxyalkylene chain. The chain may be attached to the silicon atom in any convenient way, for example by a carbon atom. Suitable hydroxyl bearing chains include those containing up to 50 chain atoms and those having 1 to 15, more preferably 4 to 10 oxyalkylene groups, which may be for example oxyethylene, oxypropylene or oxybutylene or mixtures thereof, the most preferred being the oxyethylene group. The alkylene or oxyalkylene chain may be substituted or unsubstituted and may be linear or branched. The hydroxyl group may be a primary, secondary or tertiary alcohol group. Examples of suitable groups include —CH$_2$CH$_2$CH$_2$OH, —CH$_2$CHCH$_3$CH$_2$OH, —CH$_2$CH$_2$C(CH$_3$)$_2$OH, —CH$_2$CH$_2$CH$_2$CH$_2$OH, —CH$_2$CH$_2$CH(CH$_2$OH)CH$_2$OH, —CH$_2$CH$_2$C(OH)(CH$_3$)CH$_2$CH$_3$, CH$_2$CH(OH)CH$_2$OH, —CH$_2$CH$_2$C(OH)(CH$_3$)CH$_2$CH(CH$_3$)CH$_3$, —CH$_2$CHCH$_3$CH$_2$OH, —CH$_2$CH$_3$CHCH$_2$OH, —CH$_2$CHC$_6$H$_4$OH, —CH$_2$CH$_2$CH$_2$OCH$_2$CH$_2$CH$_2$OH, —CH$_2$CH$_2$CH$_2$OCH$_2$CH(OH)CH$_2$OH, —CH$_2$CH$_2$CH$_2$OCH$_2$C(CH$_2$OH)$_2$CH$_2$CH$_3$, —CH$_2$CH$_2$CH$_2$OCH(CH$_2$OH)CH$_2$OH, —CH$_2$CH$_2$CH$_2$(OCH$_2$CH$_2$CH$_2$)$_3$OH and —(CH$_2$CH$_2$O)$_{10}$H. Polydiorganosiloxanes having hydroxyl groups also comprise siloxane units (i) as aforesaid. Other hydroxyl bearing materials which may be included as crosslinking or chain controlling agents include materials having up to three or more functional e.g. hydroxy groups per molecule for example 3,4,5 trihydroxybenzoic acid propyl ester or an arylalkylsilanol.

A composition according to the invention also comprises a fluorinated silicone foam stabilising material (D). Suitable foam stabilising materials include for example, a polysiloxane comprising

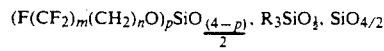

units and silicon-bonded hydroxyl groups wherein each R represents a monovalent hydrocarbon group containing from 1 to 20 carbon atoms, m is an integer having an average value of from 1 to 20, n has the value 1 or 2, p has the value 1, 2 or 3. This polysiloxane may also include from 0 to 10 percent, based on the weight of said polysiloxane, of $GSiO_{3/2}$ units wherein G represents the residue obtained by removing the hydrogen atom from a hydroxyl group of a linear organic polymer selected from the group consisting of homopolymers of ethylenically unsaturated alcohols, copolymers of these alcohols with ethylenically unsaturated hydrocarbons, polyethers and polyoxyalkylene glycols, wherein said organic polymer contains an average of at least one terminal hydroxyl group per molecule. These materials may be prepared by treatment of hexamethyldisiloxane coated polysilicates with an alcohol, for example $F(CF_2)_8CH_2OH$, and are more fully described and claimed in European Patent Specification 179 598.

Platinum catalysts (E) may take any of the known forms, ranging from platinum as deposited on carriers such as silica gel or powdered charcoal, to platinic chloride, salts of platinum and chloroplatinic acids. A preferred form of platinum is chloroplatinic acid either as the commonly obtainable hexahydrate or the anhydrous form, on account of its easy dispersibility in organosilicon systems and its non-effect on colour of the mixture. Platinum complexes may also be used e.g. those prepared from chloroplatinic acid hexahydrate and divinyl tetramethyldisiloxane. Compositions according to the invention foam and cure very rapidly when the component parts have been mixed together. We prefer to include in the composition one of the known platinum catalyst inhibitors such as a polymethylvinylsiloxane cyclic compound or an acetylenic alcohol e.g. methyl butynol.

If desired other adjuvants may be included in a composition according to the invention, for example fillers, colorants, coloured indicators, preservatives such as propyl gallate and extenders. However, in general the inclusion of fillers is not preferred.

Compositions according to the invention are formulated to be mixed in a desired hand held mixer and to be dispensed therefrom to form a foamed product on a support or on an open wound. To this end, the proportions of the ingredients are carefully selected so that the ratio of silicon-bonded hydrogen atoms of the polydiorganosiloxane (A) to all carbon bonded hydroxyl groups together with other reactive hydroxyl, unsaturated and other groups present in the composition is appropriate. This ratio may be in the range 1:1 to 20:1 and is preferably in the range 2:1 to 9:1. The ratio of aliphatically unsaturated groups to silicon-bonded hydrogen atoms is preferably in the range 0:1 to 0.5:1 more preferably in the range 0.01:1 to 0.03:1. The ratio of silicon-bonded hydrogen atoms to hydroxyl groups is suitably in the range 2:1 to 25:1 more preferably 5:1 to 11:1 We have found that compositions according to the invention in which the ingredients are present in the preferred ratios can be formulated to cure within 100 to 180 seconds of mixing of the composition at room temperature (i.e. of the order of 18° C. ± 2° C.) and humidity (i.e.) about 60% to 80% relative humidity) to provide cured foams of a density between about 40kg/m³ and 400kg/m³ or less. The foams are fine pored foams of uniform cell size. They are hydrophobic and generally comprise from about 20% to about 80% closed cells and correspondingly about 80% to about 20% open cells, the more closed cell foams being produced when increased proportions of the foam stabiliser are present. The compositions cure to a tack free condition even at those of their surfaces which lie in contact with wet surfaces.

The polydiorganosiloxane (A) is stored separated from the catalyst (E) until required for use. The component parts are packaged as two or more individually stable component parts. In a preferred arrangement, each of the parts is of substantially equal volume and viscosity so that the first and second parts may be mixed together readily in a ratio of 1:1 by volume, and each is packaged in a receptacle of material which is capable of being ruptured to release the contained component in a sterile condition for mixing with a component from another receptacle. The receptacles comprise at least a part which is capable of rupture to release the component. This part may suitably comprise a flexible, pierceable, material such as a plastics material, a soft metal or a solid gelatinous material. This part may be, for example an end wall of a tubular receptacle of another material, or an end wall of an envelope made entirely from the flexible material. The envelopes may be, for example, in the form of bellows formed of polypropylene having a reinforced base, or in the form of a stiffly resilient tube of plastics material having one end wall provided by a rupturable metal foil.

Compositions according to the invention are particularly useful in providing foamed medical dressings by application to a wound site i.e. for use in a method of treatment of the human or animal body by surgery or therapy. However, they are also suitable for numerous other applications where their rapid room temperature cure characteristics are beneficial. When used for the production of wound dressings, additives conventionally included in dressings may be included in the composition for example pharmaceuticals, biocides and growth factors.

The invention provides in another of its aspects a method of forming a foam medical dressing which comprises forming a layer of cured foamed silicone by dispensing onto a surface a mixture formed by mixing the component parts of a multi component, foam forming silicone composition each of the parts being of substantially the same viscosity and of substantially the same volume capable on admixture of its component parts of curing quickly at 20° C. to provide a foamed mass having a density of less than 400kg/m³ the composition consisting essentially of (A) one or more polydiorganosiloxanes having not less than three alkylhydrogensiloxane units per molecule, (B) one or more polydiorganosiloxanes having not less than two siloxane units of the formula

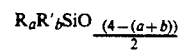

in which R represents a monovalent hydrocarbon group containing 1 to 20 carbon atoms, R' represents an unsaturated hydrocarbon group, a has the value 0, 1 or 2 and b has the value 1 or 2, (C) a liquid alcohol, (D) a fluorinated silicone foam stabilising material and (E) a platinum catalyst for promoting reaction between the components, each of the components being of substantially the same viscosity, and allowing the mixed composition to cure.

The invention provides in another of its aspects the use of a multi-component foamable silicone composition according to the invention in the preparation of a medical foam dressing.

There now follows a detailed description, to be read with the accompanying drawings, of an example composition, which is illustrative of the invention.

In the drawings:

FIG. 1 is a side elevation of a receptacle containing one component part of the example composition; and FIG. 2 is a section of the receptacle shown in FIG. 1.

The example composition was a room temperature curable foamable silicone composition comprising two components A and B of substantially equal viscosity and volume. Component A consisted of 54 parts by weight (herein all parts are parts by weight where the context permits) of a dimethylvinylsilyl endblocked polydimethylsiloxane having a viscosity of about 450 mm²/s and 0.01 mole % vinyl groups, 39 parts of a dimethylvinylsilyl endblocked polydimethylsiloxane having a viscosity of about 9,000 mm²/s and 0.002 mole % vinyl groups, 3 parts ethanol, 4 parts of chloroplatinic acid catalyst and 0.01 parts of propyl gallate. Component B consisted of 0.05 parts methyl butynol, 10 parts of dimethylvinylsilyl end blocked polydimethylsiloxane having a viscosity of about 450 mm²/s and 0.01 mole % vinyl groups, 54 parts of the dimethylvinylsilyl endblocked polydimethylsiloxane having a viscosity of about 9,000 mm²/s and 0.002 mole % vinyl groups, 16 parts of a trimethylsilyl endblocked polymethylhydrogensiloxane having a viscosity of about 30 mm²/s and 1.5 mole % hydrogen, 16 parts of a polymethylhydrogen-polydimethylsiloxane having a viscosity of about 5 mm²/s and 0.75 mole % hydrogen, 4 parts of a foam stabiliser prepared by treatment of hexamethyldisiloxane coated polysilicates with the alcohol F(CF$_2$)$_8$CH$_2$CH$_2$OH, as more fully described in European Patent Specification 179 598 and 0.01 part of propyl gallate.

The component parts A and B were packaged separately in receptacles, for example, as shown in FIGS. 1 and 2. The receptacle shown in FIGS. 1 and 2 has the shape of a cylindrical bellows (100 FIGS. 1 and 2). Each bellows is formed from polypropylene and comprises corrugated walls (102) and reinforced upper (104) and lower (106) surfaces. The construction and arrangement of the receptacle is such that its lower surface may be perforated to release the component and a comparatively light pressure is sufficient to cause controlled collapse of the bellows in the direction of its axis so that the bellows may be emptied.

That which is claimed is:

1. A multi-component, foamable silicone composition, capable on admixture of its component parts of curing quickly at 20° C. to provide a foamed mass having a density of less than 400 kg/m³ comprising (A) one or more polydiorganosiloxanes having not less than three alkyl-hydrogensiloxane units per molecule, (B) one or more polydiorganosiloxanes having not less than two siloxane units of the formula $$R_aR'_bSiO_{\frac{(4-(a-b))}{2}}$$

in which R represents a monovalent hydrocarbon group containing 1 to 20 carbon atoms, R' represents an unsaturated hydrocarbon group, a has the value 0, 1 or 2 and b has the value 1 or 2, (C) a liquid alcohol, (D) a fluorinated silicone foam stabilizing material and (E) a platinum catalyst for promoting reaction between the components, the composition being packaged as two or more individually stable parts of substantially equal volume and viscosity each in a receptacle of material which is adapted to be opened by rupture so as to release the components for admixture.

2. A composition according to claim 1 wherein the polydiorganosiloxane (A) has alkylhydrogensiloxane units of the general formula $$R_pHSiO_{\frac{(3-p)}{2}}$$

in which each R represents a monovalent hydrocarbon group containing 1 to 20 carbon atoms and p is 1 or 2 and units (i)

$$R_nSiO_{\frac{(4-n)}{2}}$$

in which R is as referred to above and n is 1, 2 or 3 and a viscosity from about 1 to about 1000 mm²/s, the unsaturated hydrocarbon group R' of the polydiorganosiloxane (B) is a vinyl, allyl, or hexenyl group, the polydiorganosiloxane (B) also comprises units (i)

$$R_nSiO_{\frac{(4-n)}{2}}$$

in which R and n are as referred to above and the polydiorganosiloxane (B) has a viscosity from about 10 mm²/s to about 25,000 mm²/s and the alcohol (C) is a lower aliphatic monofunctional alcohol having up to 8 carbon atoms.

3. A composition according to claim 1 wherein a foam stabilising material is present which comprises a material prepared by treatment of hexamethyldisiloxane coated polysilicates with the alcohol F(CF$_2$)$_8$CH$_2$CH$_2$OH.

4. A composition according to claim 1 also comprising propyl gallate.

5. A composition according to claim 1 also comprising a monofunctional silanol.

6. A composition according to claim 1 wherein the ratio of silicon bonded hydrogen atoms of the polydiorganosiloxane (A) to all carbon-bonded hydroxyl groups together with other reactive hydroxyl, unsaturated and other groups present in the composition is in the range 1:1 to 20:1, the ratio of unsaturated hydrocarbon groups to silicon-bonded hydrogen atoms is in the range 0.1:1 to 0.5:1 and the ratio of silicon-bonded hydrogen atoms to hydroxyl groups is in the range 2:1 to 25:1.

7. A composition according to claim 1 wherein at least a portion of each receptacle comprises a flexible, pierceable, plastic, soft metal or a solid gelatinous material.

* * * * *